US012004857B2

United States Patent
Biederman et al.

(10) Patent No.: US 12,004,857 B2
(45) Date of Patent: Jun. 11, 2024

(54) SENSOR HOLDER DEVICE FOR INVASIVE BIOSENSORS

(71) Applicant: DexCom, Inc., San Diego, CA (US)

(72) Inventors: William Biederman, San Francisco, CA (US); Timothy Stowe, Mountain View, CA (US)

(73) Assignee: DexCom, Inc., San Diego, CA (US)

( * ) Notice: Subject to any disclaimer, the term of this patent is extended or adjusted under 35 U.S.C. 154(b) by 922 days.

(21) Appl. No.: 17/039,804

(22) Filed: Sep. 30, 2020

(65) Prior Publication Data

US 2021/0015406 A1 Jan. 21, 2021

Related U.S. Application Data

(63) Continuation of application No. 15/362,955, filed on Nov. 29, 2016, now Pat. No. 10,827,958.

(51) Int. Cl.
*A61B 5/1473* (2006.01)
*A61B 5/00* (2006.01)
*A61B 5/145* (2006.01)

(52) U.S. Cl.
CPC ........ *A61B 5/1473* (2013.01); *A61B 5/14532* (2013.01); *A61B 5/6835* (2013.01); *A61B 5/1451* (2013.01); *A61B 5/6848* (2013.01)

(58) Field of Classification Search
CPC . A61B 5/1473; A61B 5/14532; A61B 5/6835; A61B 5/1451; A61B 5/6848; A61B 5/14865
See application file for complete search history.

(56) References Cited

U.S. PATENT DOCUMENTS

| 944,576 | A | 12/1909 | Oudinot et al. |
| 5,954,643 | A * | 9/1999 | VanAntwerp ...... A61B 5/14532 600/347 |
| 7,303,726 | B2 | 12/2007 | McAllister et al. |
| 7,343,205 | B1 * | 3/2008 | Pianca ................ A61N 1/0539 607/45 |
| 7,494,465 | B2 * | 2/2009 | Brister ................ A61B 5/6833 600/347 |
| 7,497,827 | B2 | 3/2009 | Brister et al. |
| 8,460,231 | B2 | 6/2013 | Brauker et al. |

(Continued)

FOREIGN PATENT DOCUMENTS

| CN | 106108917 A | 11/2016 |
| JP | 2012531952 A | 12/2012 |

(Continued)

OTHER PUBLICATIONS

Office Action for Chinese Application No. 201780073812.0 mailed on Apr. 22, 2021, 7 pages.

(Continued)

*Primary Examiner* — Jacqueline Cheng
*Assistant Examiner* — Tho Q Tran
(74) *Attorney, Agent, or Firm* — Snell & Wilmer LLP

(57) ABSTRACT

In some examples, a sensor holder device is described. The sensor holder device may include a rigid body, a set legs attached to the rigid body, a sensor guiding structure, a sensor retaining structure, and an electrical trace. The sensor retaining structure may be sized to accommodate a sensor wire. The electrical trace may extend proximate the sensor retaining structure and along one of the legs.

15 Claims, 11 Drawing Sheets

(56) References Cited

U.S. PATENT DOCUMENTS

| | | |
|---|---|---|
| 8,617,069 B2 | 12/2013 | Bernstein et al. |
| 8,632,731 B2 | 1/2014 | Simmons et al. |
| 8,989,833 B2 | 3/2015 | Brauker et al. |
| 9,060,742 B2 | 6/2015 | Brister et al. |
| 9,066,696 B2 * | 6/2015 | Shoshihara ........ A61B 5/14865 |
| 9,103,777 B2 | 8/2015 | Ralston et al. |
| 9,352,125 B2 | 5/2016 | Bodner |
| 9,901,713 B2 | 2/2018 | Skakoon et al. |
| 10,252,032 B2 | 4/2019 | Nelson et al. |
| 2003/0109903 A1 | 6/2003 | Berrang et al. |
| 2010/0332142 A1 | 12/2010 | Shadforth et al. |
| 2011/0077490 A1 | 3/2011 | Simpson et al. |
| 2011/0191044 A1 * | 8/2011 | Stafford ................ C12Q 1/006 |
| | | 702/65 |
| 2012/0053608 A1 * | 3/2012 | Shoshihara ........ A61B 5/14865 |
| | | 606/185 |
| 2013/0116524 A1 | 5/2013 | Cole et al. |
| 2013/0150691 A1 | 6/2013 | Pace et al. |
| 2013/0255570 A1 | 10/2013 | Brister et al. |
| 2014/0155819 A1 * | 6/2014 | Amirouche ........... A61M 5/158 |
| | | 604/82 |
| 2014/0276416 A1 | 9/2014 | Nelson et al. |
| 2015/0025345 A1 | 1/2015 | Funderburk et al. |
| 2016/0157766 A1 | 6/2016 | Simpson et al. |
| 2017/0127982 A1 * | 5/2017 | Larson ............... H01R 13/6456 |
| 2018/0146895 A1 | 5/2018 | Biederman et al. |

FOREIGN PATENT DOCUMENTS

| | | |
|---|---|---|
| JP | 2015509011 A | 3/2015 |
| JP | 7114588 B2 | 8/2022 |
| RU | 74311 U1 | 6/2008 |
| RU | 133942 U1 | 10/2013 |
| WO | WO-2007140783 A2 | 12/2007 |
| WO | WO-2016036924 A2 | 3/2016 |
| WO | WO-2018102288 A1 | 6/2018 |

OTHER PUBLICATIONS

Partial European Search Report for Application No. 17875189.7 mailed Apr. 24, 2020, 13 pages.
Examination Report No. 1 from Australian Patent Application No. 2017367026, dated Oct. 14, 2021, 4 pages.
Office Action For Japanese Application No. 2019-527872, mailed on Sep. 6, 2021, 4 pages.
International Preliminary Report on Patentability for Application No. PCT/US2017/063393 mailed Jun. 13, 2019, 7 pages.
International Search Report and Written Opinion for Application No. PCT/US2017/063393 mailed Apr. 19, 2018, 8 pages.
Katz, "Abbott Freestyle Libre CGM: 2-week trial session," Diabetes Tech Review, http://diabetestechreview.com/abbott-libre-cgm-2-week-trial-session/, Posted May 12, 2016, 9 pages.
Extended European Search Report for Application No. 17875189.7 mailed May 29, 2020, 14 pages.

* cited by examiner

SENSOR HOLDER DEVICE FOR INVASIVE BIOSENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/362,955, filed on Nov. 29, 2016. The aforementioned application is incorporated by reference herein in its entirety, and is hereby expressly made a part of this specification.

FIELD

The present disclosure generally relates to invasive biosensors and more specifically to a device for supporting sensing wires of invasive biosensors.

BACKGROUND

Invasive biosensors, such as sensors for wearable glucose monitoring devices, include thin wires that are insertable into a patient's skin. Sensing circuitry reads biological information about the patient via the thin wires. Once an invasive biosensor is inserted into a patient's skin, the electrical connections between the wires and circuitry remain exposed to potential moisture that may significantly impact the biosensor performance. For example, many electrochemical based sensors, may have performance impacts relating to calibration offsets or increases in the noise floor level due to moisture-caused current leakage within the electronics enclosure and is particularly high for biosensors included in wearable devices that may be exposed to perspiration on the patient's skin, weather, and other sources of moisture typically experienced by human skin. In addition to this consideration, the size of the device is always a practical consideration for wearables. To accommodate the required sensing circuitry, power source, and the like to process the biological information, wearable glucose monitoring devices may include multiple parts that are coupled together to form working devices. Not only does the use of multiple parts cause the devices to be bulky, but it also creates multiple areas for possible moisture ingress (e.g., seals between parts).

SUMMARY

Various examples are described relating to sensor holder devices for retaining and supporting sensor wires of invasive biosensors. For example, one disclosed device may include a rigid body, a set of legs, a sensor guiding structure, and groove formed in the rigid body, and an electrical trace. The set of legs may be attached to the rigid body and may extend from one side of the rigid body. The sensor guiding structure may be attached to the rigid body and may extend from the one side of the rigid body. The sensor guiding structure may define a guiding hole or a guiding opening. The groove may be formed in the rigid body. The groove may extend from the sensor guiding structure and may be sized to accommodate a sensor wire. The electrical trace may extend between the groove and a distal end of a first leg of the set of legs.

Another disclosed device includes a wearable monitoring device. The wearable monitoring device may include a printed circuit board, sensing circuitry, and a sensor holder device. The printed circuit board may be disposed in a housing that has an exterior surface for positioning the wearable monitoring device on a patient's skin. The sensing circuitry may include one or more electronic components coupled to the printed circuit board. The sensor holder device may include a body having a pair of legs, an electrical trace, a sensor retaining structure, and a sensor guiding structure. The pair of legs may extend from one side of the body. The sensor holder device may be physically coupled to the printed circuit board via the pair of legs. The electrical trace may extend along a first leg of the pair of legs to a first distal end of the first leg. The electrical trace may electrically couple a sensor wire to the printed circuit board. The sensor retaining structure may be disposed on the body and may retain a proximal portion of the sensor wire proximate to the electrical trace. The sensor guiding structure may guide a distal portion of the sensor wire beyond the exterior surface of the housing.

One disclosed system may include a sensor wire and an interposer device. The sensor wire may include a first portion insertable into a patient's skin. The first portion may include means for generating glucose information. The interposer device may include sensor positioning means, retaining means, and coupling means. The sensor positioning means may be for positioning the sensor wire such that an insertion needle can insert the first portion into the patient's skin. The retaining means may be fore physically retaining a second portion of the sensor wire. The coupling means may be for electrically coupling the second portion of the sensor wire to circuitry disposed on a printed circuit board for determining a glucose level for a patient.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
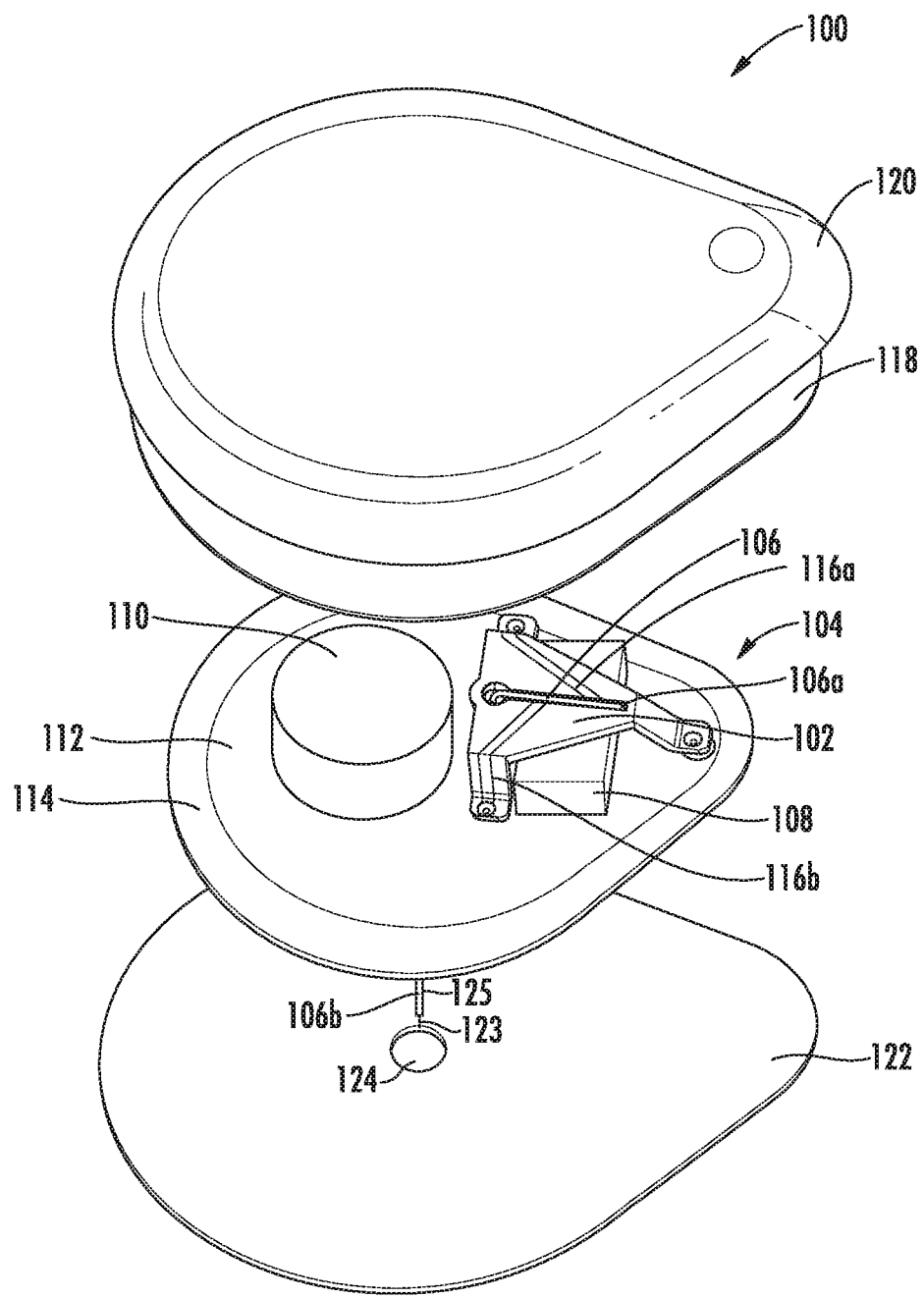
FIG. 1 illustrates an exploded, perspective view of an example of a monitoring device including a sensor holder device, according to at least one example.

Examples are described herein in the context of sensor holder devices for use in continuous monitoring devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a wearable glucose monitoring device includes a glucose sensor that can be inserted into a person's skin for continuous monitoring of the person's glucose levels. While being worn, the wearable glucose monitoring device may be exposed to normal external forces resulting from clothing, bumping up against obstacles, and other external forces. To reduce the impact of these forces and to improve wearer comfort, the footprint and the profile of the glucose monitoring device may be reduced. As a way to do so, the glucose monitoring device described herein includes a sensor holder device. The sensor holder device has a unique shape that enables it to perform various functions, while also efficiently utilizing space in the glucose monitoring device. The unique shape is defined by a body that is supported by legs that extend from the body form void below the body. The legs are connected to a printed circuit board ("PCB") below the body and function to space the body apart from the PCB. Components of the glucose monitoring device such as an integrated circuit and/or other sensing circuitry may be installed below the body, within the void. In this manner, the sensor holder device provides for efficient use of space in the glucose monitoring device (e.g., allows for stacking of components and reduces an overall footprint of the device).

The functions performed by the sensor holder device include structurally supporting electrodes of the glucose sensor, aligning sensor wires of the glucose sensor toward the person's skin, and electrically connecting the electrodes to the PCB. The sensor holder device structurally supports the electrodes by way of a groove into which the electrodes are placed. The sensor holder device aligns the sensor wires by way of a cylindrical opening or against one of the legs, either of which extends from the body of the sensor holder device toward the underside of the device. The sensor holder device electrically connects the electrodes by way of electrical traces formed in the surface of the sensor holder device. The electrical traces can extend between the groove and down the legs to the PCB. While the sensor holder device is described herein with reference to a glucose monitoring device, it is understood that the sensor holder device may be implemented to support any suitable electromechanical sensor.

Turning now to the figures, FIG. 1 illustrates a monitoring device 100, according to at least one example. The monitoring device 100 includes a sensor holder device 102 and a biosensor 104 such as a glucose sensor or other electromechanical sensor for use in sensing biological information of a patient. The biosensor 104 includes a sensor wire 106, sensing circuitry 108, a power source 110 such as a battery, a printed circuit board ("PCB") 112, and an antenna 114. The sensor wire 106 includes a proximal end portion 106a and a distal end portion 106b. The proximal end portion 106a is supported by the sensor holder device 102. For example, the proximal end portion 106a may be disposed within a groove or channel of the sensor holder device 102. The proximal end portion 106a is also electrically connected to the PCB 112 via the sensor holder device 102. For example, as described in detail herein, the sensor holder device 102 may include a set of electrical traces 116a, 116b that extend proximate to a middle area of the sensor holder device 106 toward the PCB 112. When in use, the distal end portion 106b is injected into a patient's skin to measure biological parameters (e.g., glucose levels) in the interstitial fluid of subcutaneous tissue beneath the skin.

The monitoring device 100 also includes a moisture barrier 118 disposed between a top enclosure 120, such as a cap, and a bottom enclosure 122. When assembled, the moisture barrier 118 may create a seal that keeps moisture from infiltrating the biosensor 104. When assembled, the top enclosure 120 encloses the biosensor 104 and the sensor holder device 102 and mates with the bottom enclosure 122. The bottom enclosure 122 includes an opening 124 through which the distal end portion 106b passes, when installed. The PCB 112 may include a corresponding opening through which the distal end portion 106b passes. On the opposite side shown, the bottom enclosure 122 may include a substantially planar surface to allow the monitoring device 100 to be placed on the person's skin.

The sensor holder device 102 may be suitably rigid to support the sensor wire 106 and provide structural support to the PCB 112. For example, the sensor holder device 102 may be formed from liquid crystal polymer. In some examples, the PCB 112 may be a flexible printed circuit board ("FPCB"). In this example, attaching the sensor holder device 102 to the PCB 112 may add rigidity to the entire monitoring device 100, in addition to the FPCB 112.

The sensor holder device 102 may be considered an interposer device. For example, because the sensor holder device 102 stands off from the PCB 112 and may stand above components (e.g., the sensing circuitry 108, the power source 110, etc.) disposed below it, the sensor holder device 102 functions to save space within the monitoring device 100. This may result in the monitoring device 100 having a smaller footprint. In addition, because of the configuration of the sensor holder device 102 with respect to the PCB 112, the PCB 112 may be placed close to the person's skin unlike other monitoring devices that include a standoff fixture. This provides for improved wearer comfort and less overall device bulkiness.

The sensor wire 106 may include one or more electrodes, chemicals, or other means for generating biological information. For example, the sensor wire 106 may be a co-axial sensor and include two electrodes 123, 125 that are inserted into the person's skin to expose the electrodes 123, 125 to the interstitial fluid in the person's subcutaneous tissue. The electrode 123 includes at least a portion of the sensor wire 106 made of platinum or having a platinum coating and electrode 125 includes a silver/silver-chloride ("Ag/AgCl") material that covers a part of electrode 123. The electrodes 123, 125 may be used to generate glucose information about the patient by generating electrical signals corresponding to an amount of glucose present within the interstitial fluid. In some examples, a reactive material, such as glucose oxidase ("GOX"), may also be coated on a distal end of the electrode 123 to create reaction products with glucose present in the interstitial fluid. When a voltage is applied to the electrodes 123, 125, an electrical current is generated based on the amount of these reaction products generated by the glucose/GOX reaction. The electrical current is routed through the sensor wire 106 to the sensing circuitry 108. The sensing circuitry 108 may use the strength of the current to determine glucose information such as the patient's glucose levels. Although glucose level measurements are described in this example, the biosensor 104 may be configured to measure other biological parameters without departing from the scope of the present disclosure. Similarly, while the chemical materials applied onto the sensor wire 106 to form the electrodes 123, 125 and the reactive material coated onto the electrodes 123, 125 may be suitable for a glucose sensor, other material may be used according to other examples, based on the application of the biosensor 104.

The sensor wire's 106 length may allow the sensor wire 106 to extend from beneath the person's skin to the sensor holder device 102 with allowance for the patient's movement. For example, the sensor wire 106 may be between approximately 10 millimeters to 30 millimeters long. The sensor wire's 106 thickness, or gauge, may be selected to allow the sensor wire 106 to remain injected into the skin during this period with minimal discomfort. In some examples, the sensor wire 106 includes an outer diameter of approximately 100-200 microns for portions of the wire coated with the electrode 125 and an outer diameter of approximately 100 microns for the electrode 123. In additional examples, the sensor wire 106 generally may have a maximum outer diameter approximately between 100 microns and 300 microns. In some examples, however, the sensor wire 106 may have an outer diameter of about 50 microns.

In some examples, the sensing circuitry 108 includes one or more electronic components configured for signal processing. For example, the sensing circuitry 108 may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, voltage regulators, and/or any other suitable component. The sensing circuitry 108 may be configured to receive electrical signals from the sensor wire 106 (e.g., via the PCB 112 and the electrical traces 116) and process the electrical signals to determine glucose levels of the patient.

In some examples, the sensing circuitry 108 includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from electrodes 123, 125 of the sensor wire 106. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform the steps described herein as carried out, or assisted, by a processing device. Examples of computer-readable media may include, but are not limited to a memory chip, ROM, RAM, ASIC, or any other storage means from which a processing device can read or write information.

The top enclosure 120 and the bottom enclosure 122 may together form a housing for retaining the biosensor 104. The housing may be compact in size for placing on the person's skin. The housing may be made of any suitable material for housing the biosensor 104. Non-limiting examples of materials that may be suitable for the housing include silicone, polyethylene, polyvinyl chloride ("PVC"), polypropylene, nylon, polyurethane, polycarbonate, steel, aluminum, and other plastics and metals. The monitoring device 100 may be secured to the skin using an adhesive, band, strap, or other securing means. In some examples, the monitoring device 100 may be worn for extended period of time (e.g., days, weeks, months, etc.).

Figure 2:
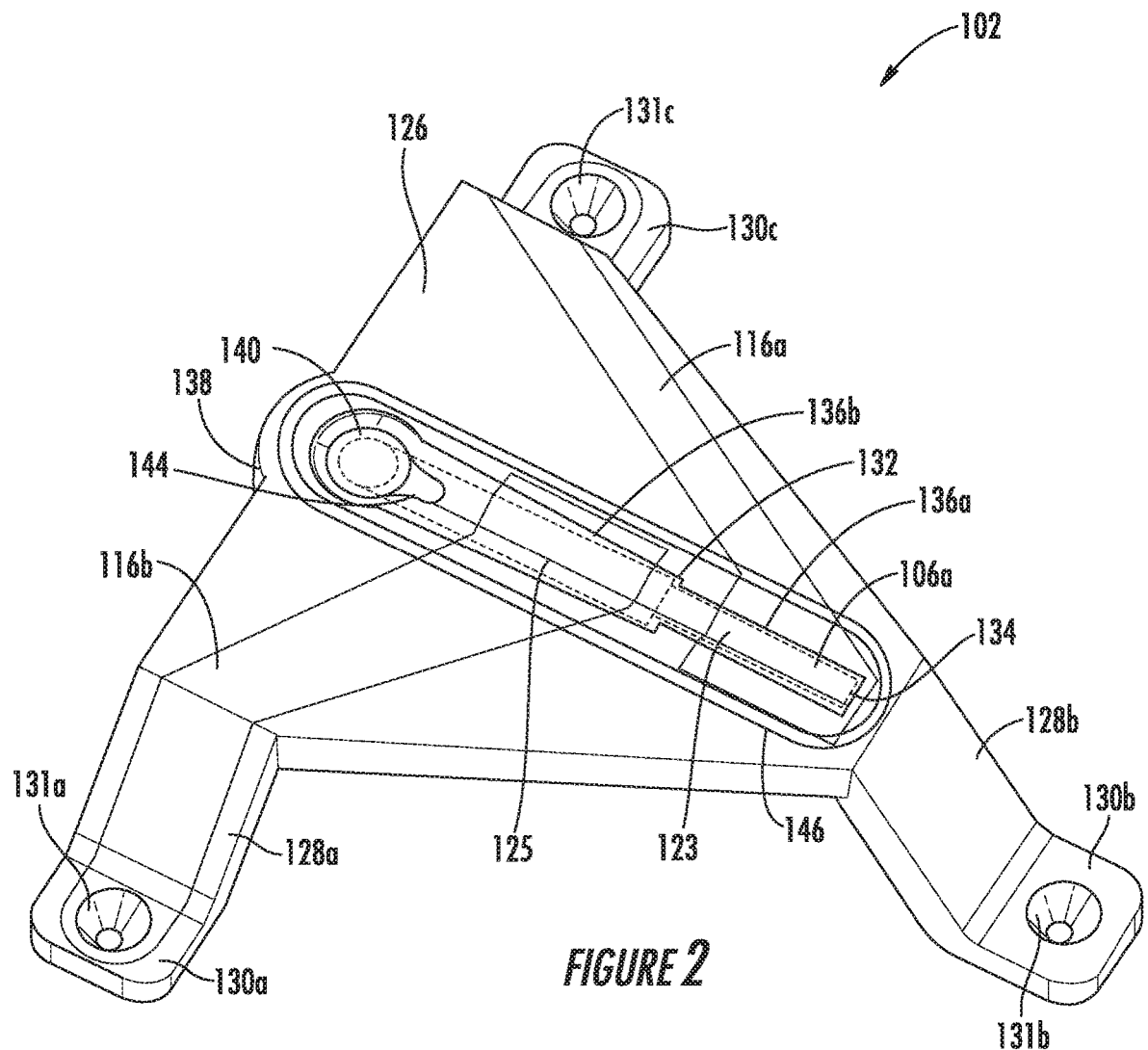
FIG. 2 illustrates a top, perspective view of an example of a sensor holder device, according to at least one example.
Figure 3:
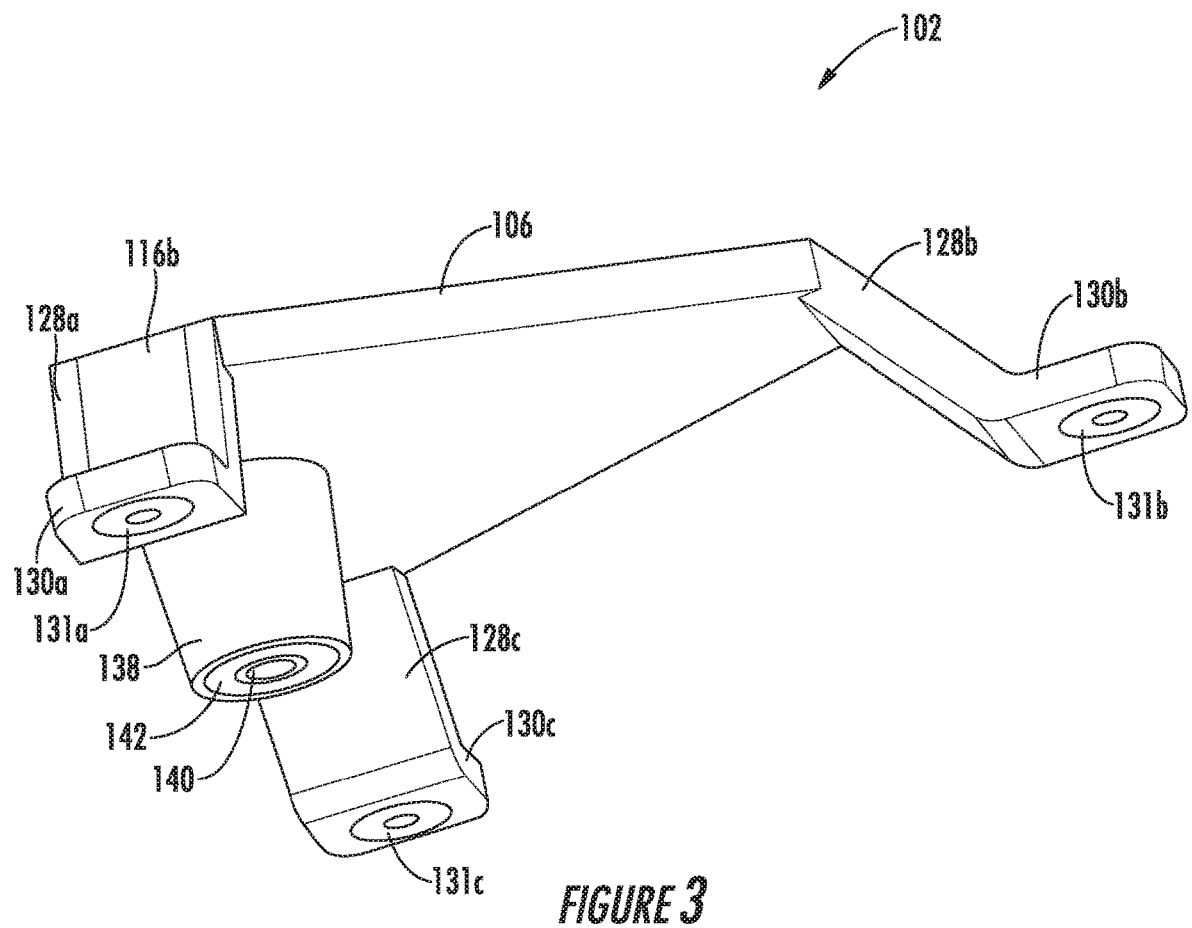
FIG. 3 illustrates a bottom, perspective view of an example of a sensor holder device, according to at least one example.
Figure 6:
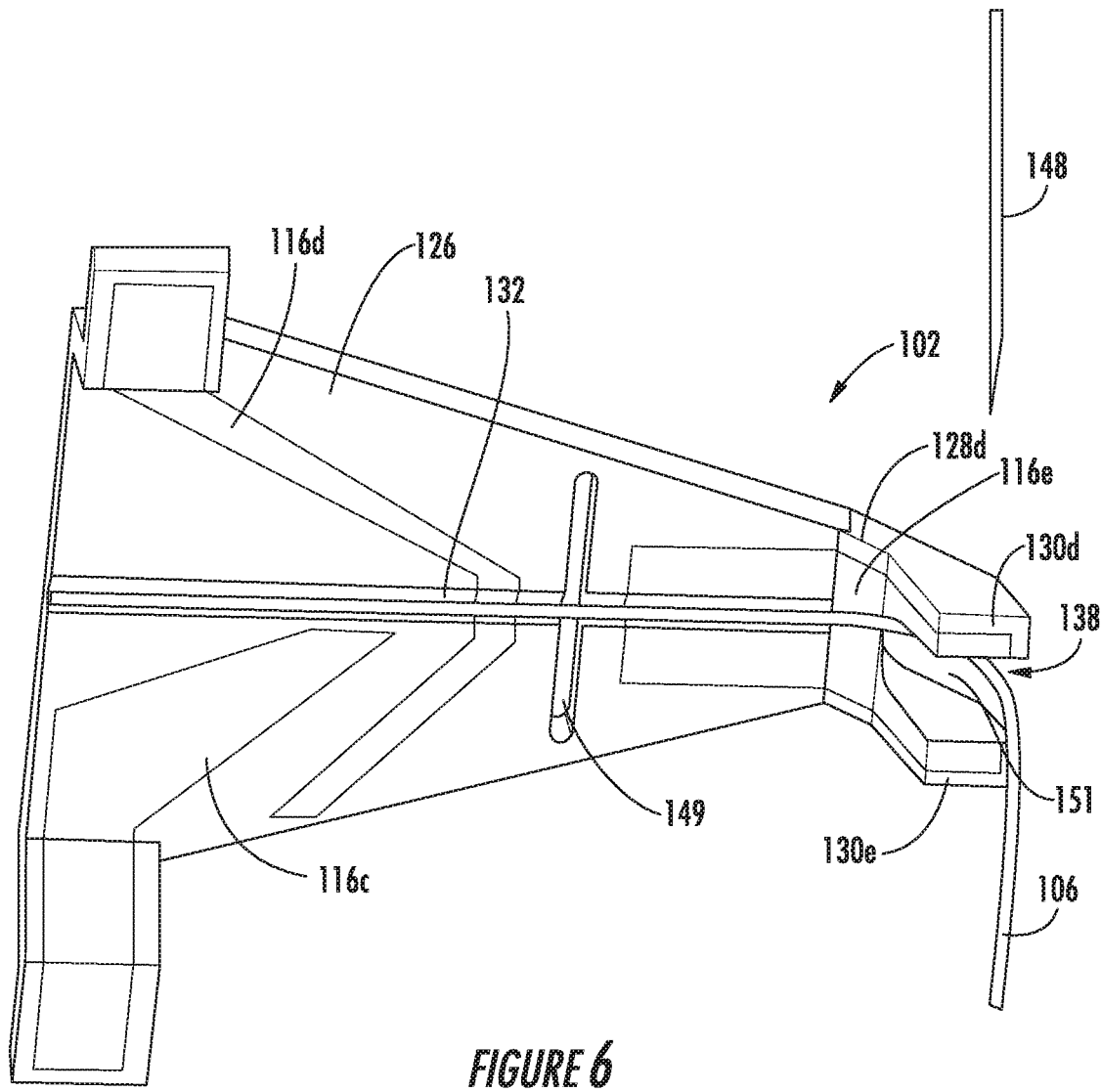
FIG. 6 illustrates a bottom, perspective view of an example of a sensor holder device, according to at least one example.

FIGS. 2 and 3, respectively illustrate a top perspective view and a bottom perspective view of the sensor holder device 102, according to certain examples. The sensor holder device 102, which is a type of molded interconnect device, may include a body 126 and a set of legs 128, a few of which are illustrated (e.g., 128a, 128b). The body 126 may include a substantially planar topside area (e.g., greater than 1 mm 2). This topside area may be suitable sized and suitably flat to allow a suction head of a robotic placement device (e.g., a pick and place device) to grasp the sensor holder device 102. For example, the topside area may be located adjacent to the retaining structure 132 and a perimeter edge of the body 126. When the retaining structure 132 is disposed on an underside of the body 126 (e.g., as shown in FIG. 6), the topside area may be located at any suitable location along the topside of the body 126. Thus, the topside area may be greater when the retaining structure 132 is disposed on the underside of the body 126. This may result in more suitable locations where the suction head can pick up the sensor holder device 102 as compared to examples where the retaining structure is disposed on the topside of the body 126.

In some examples, the sensor holder device 102 may have a height of about 3 mm, a width of about 15 mm, and a length of about 20 mm. In other examples, the height, width, and/or length of the sensor holder device 102 may be respectively greater than or less than 3 mm, 15 mm, and/or 20 mm. The height of about 3 mm may be selected to be less than the height of the power source 110. The height of about 3 mm may also provide a suitable separation between the proximal end of the sensor wire 106b and the sensing circuitry 108 and other electronic components attached to or otherwise disposed within the PCB 112.

The set of legs 128 extend from one side of the body 126, extend below the body 126, and, in some examples, include a corresponding set of feet 130, a few of which are illustrated (e.g., 130a-130c). For example, the body 126 may be oriented in a first plane and the set of feet 130 may be oriented in a second, different plant. The set of legs 128 may extend between the first plane and the second plane to connect the body 126 to the set of feet 130. The body 126 may be oriented in the first plane when a substantial portion of the body 126 is located in the first plane. The set of feet 130 (e.g., distal ends of the set of legs 128) may be oriented in the second plan when substantial portions of the set of feet are located in the second plane. In some examples, the feet 130 may include solder rings 131, a few of which are illustrated (e.g., 131a-131c). The sensor holder device 102 may be electrically and structurally attached to a PCB (e.g. the PCB 112) or other structure using the solder rings 131. For example, the electrical traces 116, which begin in the body 126 and extend along the legs 128 and into the feet 130, may be electrically connected to the PCB 112 via the solder rings 131. In some examples, the feet 130 are connected to the PCB 112 using surface mount technology.

The sensor holder device 102 may be formed in any suitable manner including, for example, injection molding, or other suitable techniques. The sensor holder device 102 may be formed as a single piece including at least the body 126, the legs 128, the feet 130, and/or a sensor retaining structure 138. The sensor holder device 102 may be formed from any suitable material including, for example, liquid crystal polymer (e.g., RTP 3499-3 X 113393 A sold by RTP Co., VECTRA® E840i LDS sold by Ticon, etc.), high-temperature nylon, polyetheretherketone ("PEEK"), and other similar materials. In some examples, the material selected for the sensor holder device 102 may be non-conductive, may be compatible with soldering, have low moisture absorption properties, have low water vapor transmission rates, and may be easily moldable into very thin walls. In some examples, the material selected for the sensor holder device 102 may be capable of laser direct structuring ("LDS") processing. The rigidity of the sensor holder device 102 may depend on one or both of the sensor holder device's 102 thickness and the material forming the sensor holder device 102. For example, the sensor holder device's 102 thickness may be inversely proportional to the density of the material (e.g., a denser material may allow for a thinner sensor holder device 102 while a less dense material may require a thicker sensor holder device 102).

The sensor holder device 102 also includes a sensor retaining structure 132 disposed in a top surface of the body 126. In this example, the sensor retaining structure 132 may include a groove (e.g., having a U-shaped, V-shaped, etc. cross-section) sized to receive the sensor wire 106 (shown in dashed lines). In addition to or instead of the groove, the sensor retaining structure 132 may include any suitable combination of tabs, hooks, springs, and the like configured to retain the sensor wire 106. In some examples, the sensor retaining structure 132 may be used to align the sensor wire 106 during assembly. For example, the proximal end portion 106a of the sensor wire 106 may be brought into contact with an end wall 134 near a first region 136a of the sensor retaining structure 132. This may align the sensor wire 106 in the transverse direction. Similarly, because the sensor wire 106 may sit down in the sensor retaining structure 132, the sensor retaining structure 132 may align the sensor wire 106 in the lateral direction.

In some examples, the sensor retaining structure 132 may be defined to include the first region 136a and a second region 136b. The electrical trace 116a may extend proximate to and, in some examples, within the first region 136a. Likewise, the electrical trace 116b may extend proximate to and, in some examples, within the second region 136b. In some examples, a first dimensional measurement (e.g., a width, a depth, a cross-sectional area, etc.) taken laterally across the sensor retaining structure 132 in the first region 136a may be different from a second dimensional measurement taken laterally across the sensor retaining structure 132 in the second region 136b. These differences may be included in the sensor retaining structure 132 to accommodate the electrodes 123, 125. As described herein, the electrodes 123, 125 may be of different sizes (e.g., have different diameters). The different lateral measurements may be selected based on the respective widths of a proximate end of the sensor wire at different locations. For example, one portion of the proximate end of the sensor wire may be an exposed platinum electrode 123, which may have a narrower gauge than another portion which includes the platinum wire coated with a silver/silver-chloride electrode 125.

In some examples, the sensor holder device 102 may include other components (e.g., electronics, antennas, etc.) attached to or otherwise formed in the body 126 and/or the legs 128 For example, an antenna may be printed on the body 126 and electrically coupled to other electronics (e.g., an electronic device attached to the sensor holder device 102, the sensing circuitry 108, and/or the PCB 112) via one or more electrical traces, such as the electrical traces 116.

In some examples, the sensor holder device 102 may include any suitable number of electrical traces 116 to support any suitable number of electrodes. For example, both electrical traces 116a, 116b may extend along the leg 128a (e.g., on the same side of the leg 128a or on opposite sides). In this example, other electrical traces 116 may extend along the other legs 128 of the sensor holder device 102. For example, two or more electrical traces 116 may extend along each of the legs 128a-128c. In some examples, at least one of the electrical traces 116 may function as a guard trace to reduce current leakage of one or more other electrical traces 116.

The electrical traces 116a, 116b may be formed in the sensor holder device 102 using any suitable technique. Examples of such techniques include LDS processing and corresponding techniques for depositing a conductive material such as copper, nickel, gold, etc. in a circuit pattern. Such techniques may include electroless copper plating. For example, such techniques may include those using Enplate® LDS AG-600 as sold by Enthone®. The electrical traces 116a, 116b may have a thickness of about 1 micron. In some examples, the electrical traces 116a, 116a have a thickness of less than 1 micron (e.g., 0.25 microns to 0.5 microns).

The electrodes 123, 125 may be electrically connected to the electrical traces 116a, 116b in any suitable manner. For example, once the electrodes 123, 125 have been placed in the sensor retaining structure 132, a conductive pressure sensitive adhesive ("PSA") or other electrically conductive adhesive may be applied to the electrodes 123, 125. The electrically conductive adhesive may form independent electrical connections between the electrodes 123, 125 and the electrical traces 116a, 116b. In some examples, the electrically conductive adhesive may be in any suitable form such as liquid, film, tape, and the like. Examples of suitable materials include Electrically Conductive Adhesive Transfer Tapes ("ECATT") sold by the 3M, ARclad® brand PSAs such as 8001-75, 8001-77, 9032, or 9032-70 sold by Adhesives Research®, Supreme 10HTFN sold by the Master-Bond®, or any other suitable material. Such electrically conductive adhesives may be considered "snap cure" epoxies, polyurethanes, B-stage films, and the like.

The sensor holder device 102 also includes a sensor guiding structure 138. The sensor guiding structure 138 is attached to the body 126 and extends away from the body 126 in generally the same direction as the legs 128. The sensor guiding structure 138 can be attached to the body 126 by being formed directly from the body 126. The sensor guiding structure 138 may also be attached to the body 126 by being formed as a separate part and connected to the body 126. The sensor guiding structure 138 may include an opening or hole 140 through which the sensor wire 106 may pass. The hole 140 may have any suitable shape such as cylindrical, conical, rectangular, and the like. Thus, the cross-section of the hole 140 may change with respect to its depth.

Like the feet 130, the sensor guiding structure 138 may be attached to the PCB 112 using surface mount technology. For example, the sensor guiding structure 138 may include a solder ring 142, which during solder reflow creates a hermetic seal between the sensor guiding structure 138 and the PCB 112. During manufacturing, the sensor wire 106 may be threaded through the PCB 112 and the hole 140 before being bent into place within the sensor retaining structure 132.

In some examples, a potting material 144 may be positioned proximate the sensor wire 106 within the hole 140 as shown in FIG. 2. For example, the potting material 144 may be injected on top of and around the sensor wire 106 to pot the sensor wire 106 to the hole 140. In some examples, the potting material 144 may include a non-conductive material to prevent a short in the sensor wire 106. The potting material 144 may provide a moisture barrier for the electrical connections between the electrical traces 116 and the electrodes 123, 125. Non-limiting examples of the potting material 144 include epoxy, wax, silicone, acrylic, polyurethane, or other means for providing a moisture barrier. Although the potting material 144 is shown as positioned only proximate to the sensor wire 106, the potting material 144 may be applied to coat other components of the sensor holder device 102.

In some examples, a moisture seal 146 may be formed along a topside surface of the sensor holder device 102. The moisture seal 146 may function as a moisture barrier between the body 126 and the top enclosure 120. The moisture seal 146 may be formed by seam welding the top enclosure 120 to the body 126, with the sensor retaining structure 132 disposed within the moisture seal 146. For example, a portion of the body 126 may be melted together with a portion of the top enclosure 120, or a moisture barrier adhesive may be applied to the body 126 prior to installation of the top enclosure 120. In some examples, the adhesive may be pressure activated, and set when an installation force is applied to the top enclosure 120 to install it on the body 126.

Figure 4:
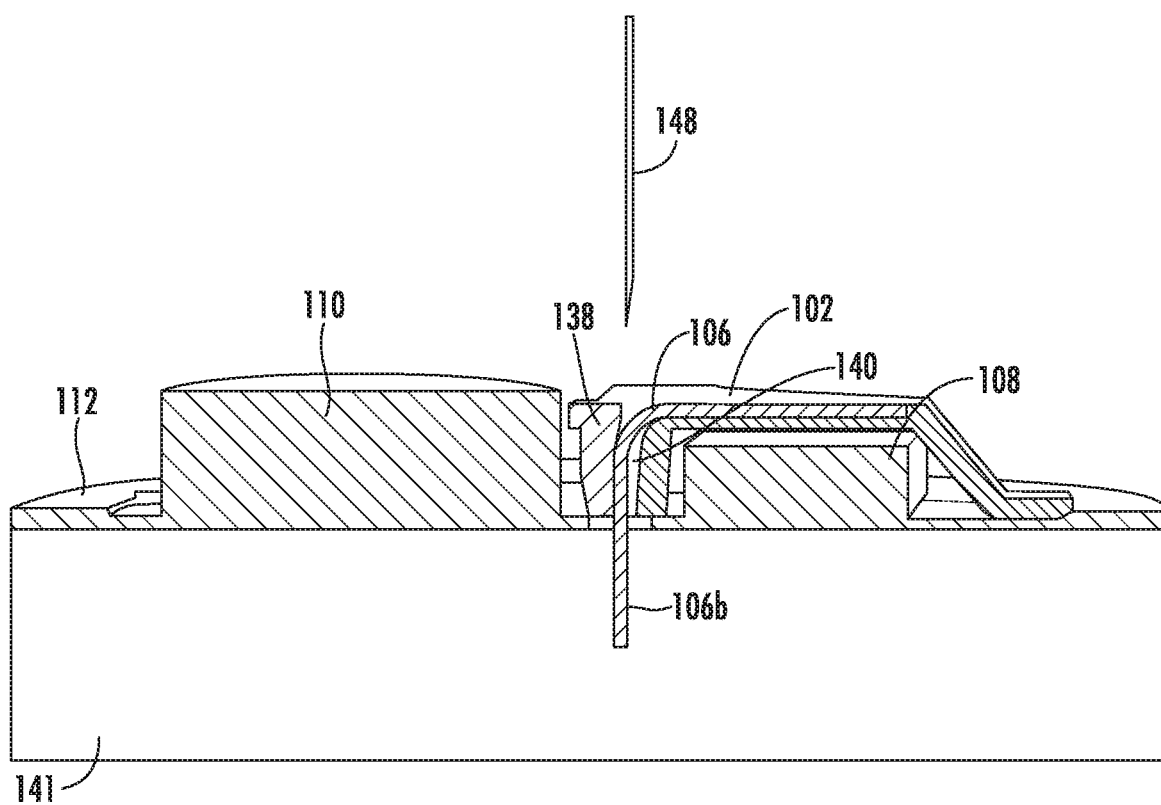
FIG. 4 illustrates a side, cross-sectional view of an example of a sensor holder device, according to at least one example.
Figure 5:
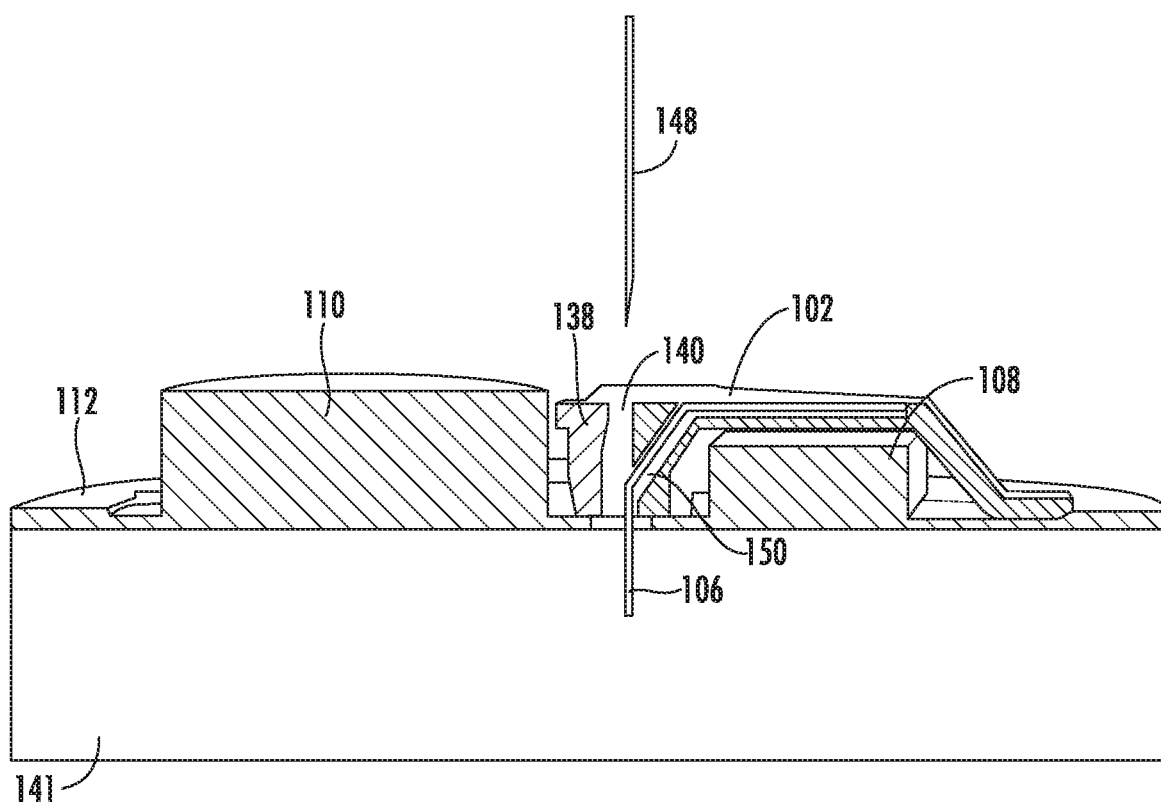
FIG. 5 illustrates a side, cross-sectional view of an example of a sensor holder device, according to at least one example.

FIGS. 4 and 5 illustrate examples of the sensor holder device 102, according to certain examples. As illustrated in FIG. 4, during insertion of the distal end portion 106b into a person's skin 141, the hole 140 or a separate opening that intersects with the hole 140, may be used to align a hypodermic insertion needle 148 of a sensor insertion tool (not shown). For example, placing the insertion needle 148 in the hole 140, with the monitoring device 100 pressed against the person's skin 141, may achieve the proper alignment for the insertion needle 148 to insert the sensor wire 106 into the person's skin 141.

While the sensor guiding structure 138 in FIGS. 3 and 4 is illustrated as extending about orthogonally away from the body 126, it is understood that the sensor guiding structure 138 may be connected to the body 126 at any other suitable angle and/or may include other openings. For example, as illustrated in FIG. 5, the sensor guiding structure 138 may also include a sensor hole 150. In this example, the hole 140 may be considered a guiding hole for receiving, guiding, and aligning the insertion needle 148. The sensor hole 150, on the other hand, may function to guide the sensor wire 106 from the body 126 to a location beyond the PCB 112. In some examples, the angle between the sensor hole 150 and the hole 140 may help stabilize the sensor wire 106 in the insertion needle 148 during insertion. For example, threading the sensor wire 106 through the sensor hole 150 may cause the sensor wire 106 to press up against the insertion needle 148.

FIG. 6 illustrates an example of the sensor holder device 102 that includes the sensor retaining structure 132 (e.g., a groove or comparable structure described herein) disposed on an underside of the body 126, according to at least one example. Thus, in this example, the sensor wire 106 is retained by the sensor retaining structure 132 on the underside of the body 126. In some examples, placing the sensor wire 106 on the underside of the body 126 may result in additional mechanical protection (e.g., provided by the sensor holder device 102) and additional moisture protection (e.g., from being located further within the monitoring device 100). In addition, placing the sensor wire 106 on the underside of the body 126 may result in decreased manufacturing costs and increased throughput. For example, because all electrical traces are located on the same side of the sensor holder device 102 (e.g., no requirement for through plating), the sensor holder device 102 does not have to be turned over during manufacturing.

In the illustrated example, the sensor holder device 102 includes electrical traces 116c-116e also disposed on the underside of the body 126. The electrical traces 116c-116e are examples of the electrical traces 116a, 116b. In some examples, each of the electrical traces 116c-116e correspond to an electrode of the sensor wire 106. In other examples, the electrical trace 116d may be a guard trace, which may be installed in the sensor holder device 102 to reduce current leakage between the electrical traces 116c and 116e. In some examples, the sensor holder device 102 may also include an isolation slot 149. The isolation slot 149 may be formed in the sensor holder device 102 to reduce current leakage between the electrical traces 116. In some examples, the isolation slot 149 may be injected with potting materials (e.g., petroleum jelly, paraffin wax, low temperature silicones, etc.) to provide additional electrical protection against leakage currents.

In the illustrated example, the sensor guiding structure 138 may be defined by one of the legs 128. Thus, instead of including a separate structure, the sensor guiding structure 138 may be defined by the leg 128d that includes a contoured shape including a guiding opening 151. The guiding opening 151 may be used to guide the sensor wire 106 from the body 126 towards the underside of the sensor holder device 100. The guiding opening 151 may be defined as being disposed between two feet, 130e and 130d, of the leg 128d. In some examples, the leg 128d may include a single foot 130 including a guiding hole such as the guiding hole 140. In any event, the leg 128d, including the guiding opening 151, may guide the sensor wire 106 from the sensor retaining structure 132 toward the underside of the sensor holder device 100. In this example, the insertion needle 148 may be inserted through the guiding opening 151 to intersect with the sensor wire 106 as part of inserting the sensor wire 106 into the person's skin.

Figure 7:
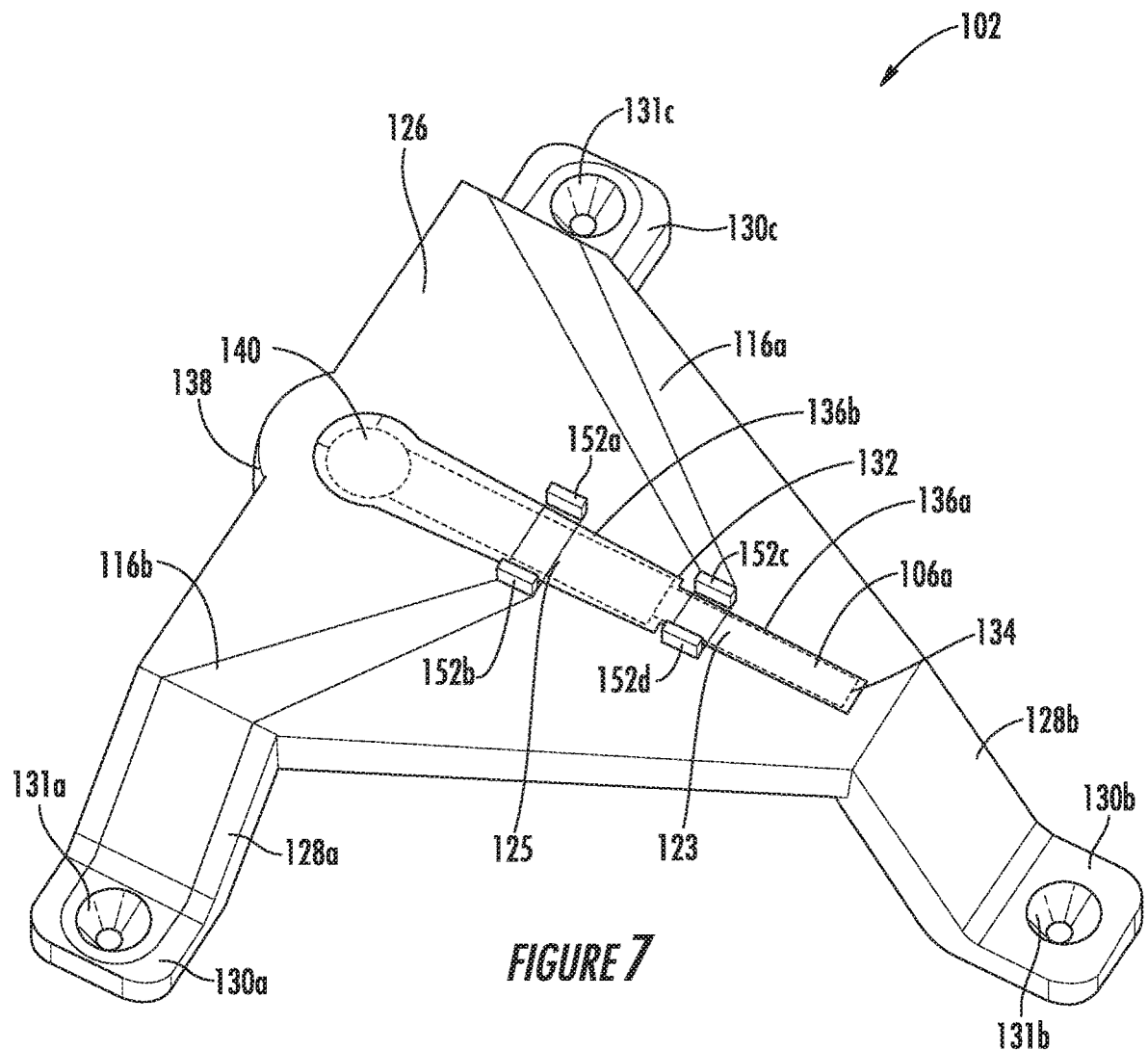
FIG. 7 illustrates a top, perspective view of an example of a sensor holder device, according to at least one example.

FIG. 7 illustrates an example of the sensor holder device 102 including a sensor retaining structure 132, according to at least one example. The sensor retaining structure 132 illustrated in FIG. 7 includes a set of tabs 152 (e.g., 152a-152d) configured to retain and align the sensor wire 106. The tabs 152 may be suitable spaced apart to receive and retain the sensor wire 106 via a snap-fit. For example, the tabs 152 may include grooves formed on inward-facing surfaces. Additionally, the tabs 152 may be configured to deflect laterally in response to a downward force. For example, during installation, a downward force may be applied to the sensor wire 106 in the direction of the top surface of the body 126, with the sensor wire aligned between the tabs 152a, 152b and 152c, 152d. This downward force may cause the tabs 152 to defect slightly laterally to accommodate the sensor wire 106 at least until the sensor wire 106 reaches the grooves formed on the inward-facing surfaces of the tabs 152.

As illustrated in FIG. 7, the electrical traces 116 may extend between the sensor retaining structure 132 and the feet 130. In some examples, the electrical traces 116 may extend within the tabs 152. In this manner, electrical connections between the electrical traces 116 and the sensor wire 106 may be made within the inward-facing surfaces of the tabs 152.

As introduced herein, the sensor retaining structure 132 may, in some examples, include hooks configured to retain the sensor wire 106. The sensor retaining structure 132 may also include springs, such as overmolded leaf springs, configured to retain the sensor wire 106. Any of the variations of the sensor retaining structure 132 described herein may be used in combination with the PSAs described herein.

Figure 8A:
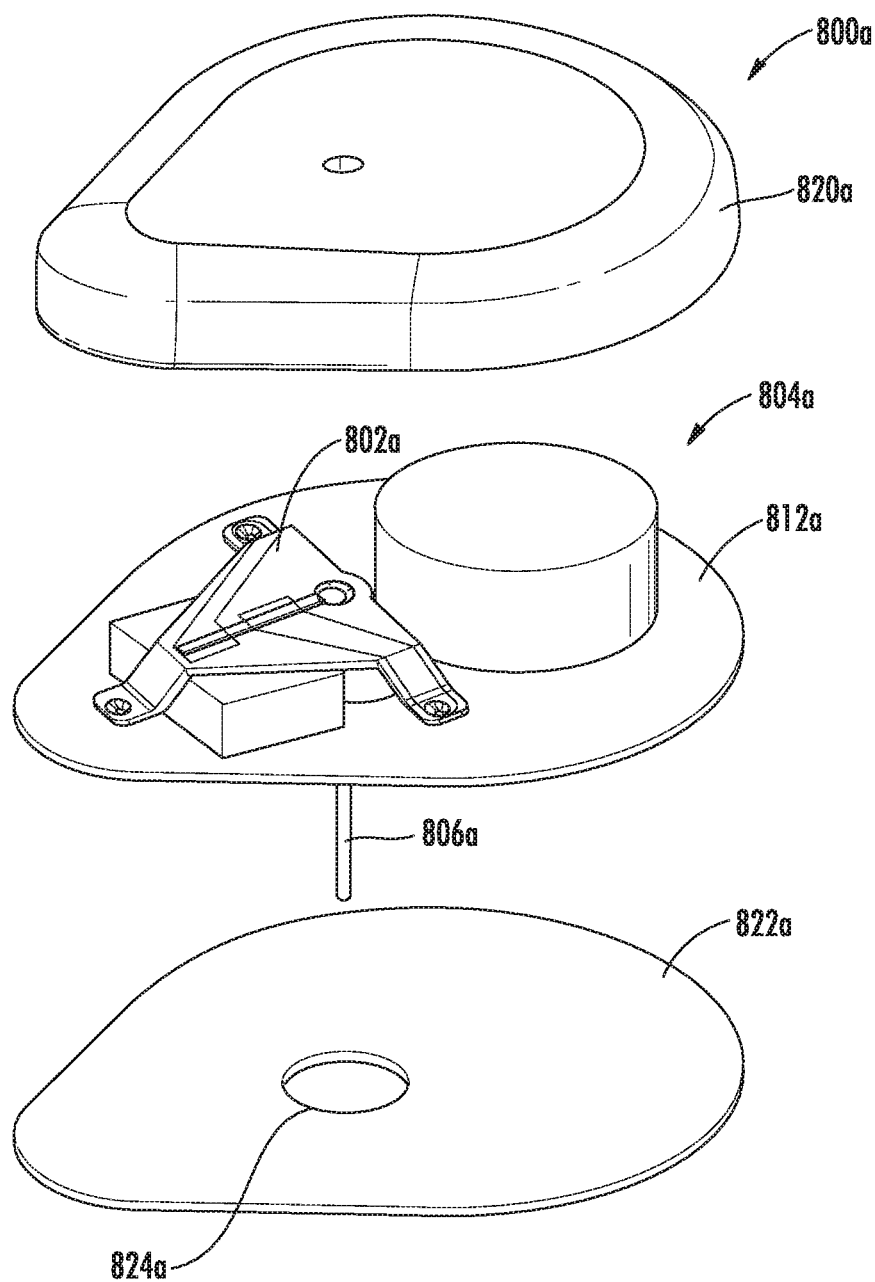
FIG. 8A illustrates an exploded, perspective view of an example of a monitoring device including a sensor holder device, according to at least one example.
Figure 8B:
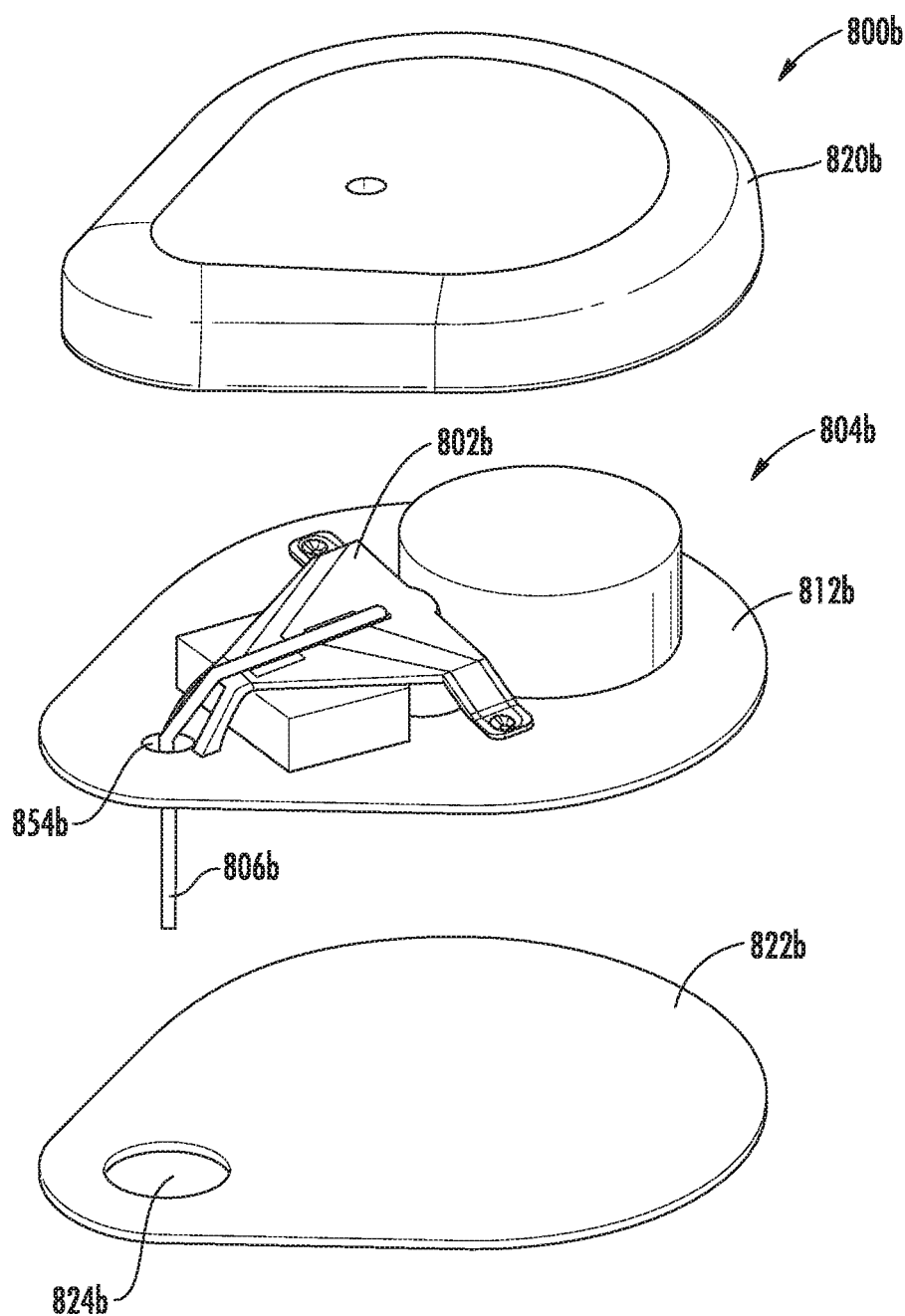
FIG. 8B illustrates an exploded, perspective view of an example of a monitoring device including a sensor holder device, according to at least one example.
Figure 8C:
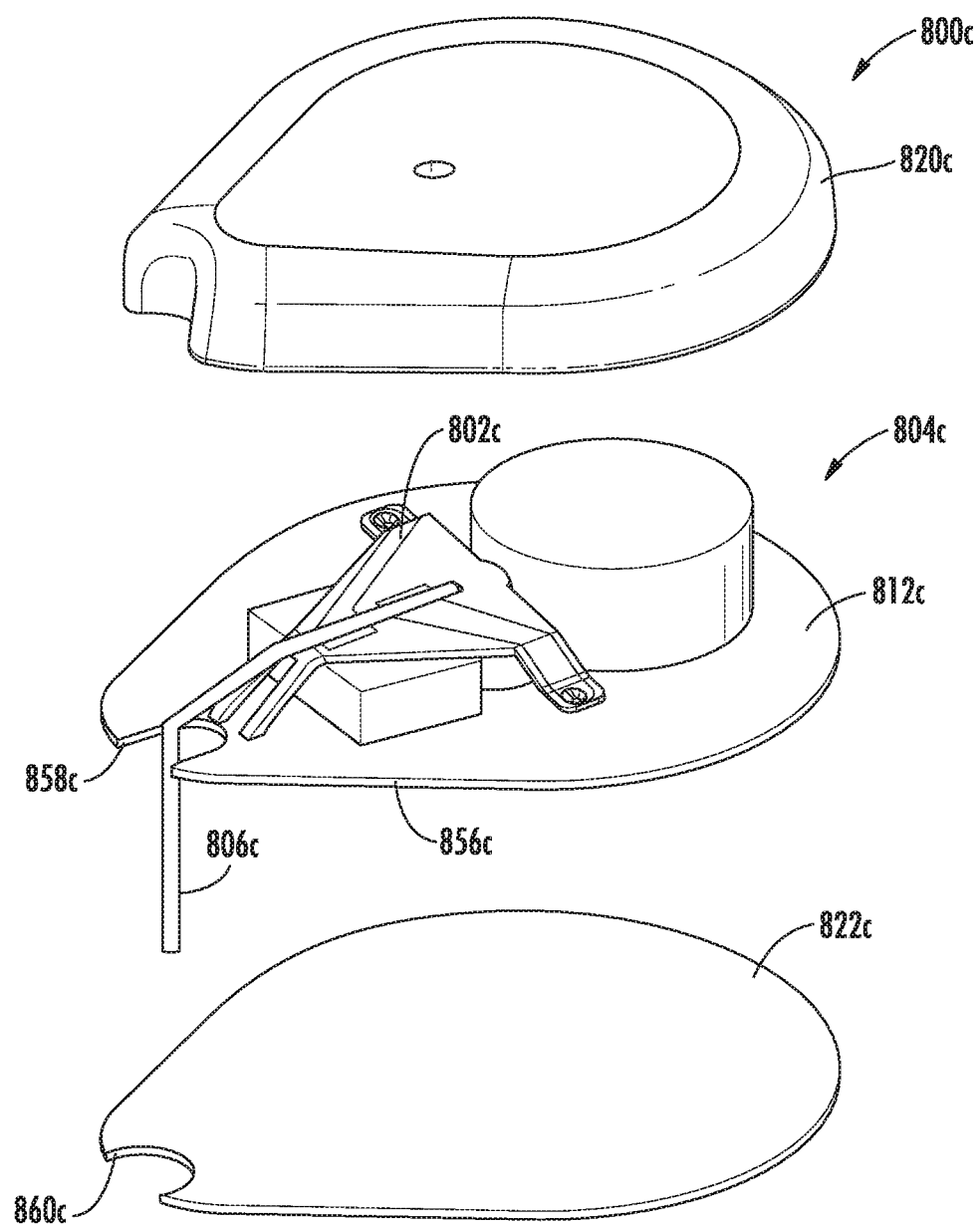
FIG. 8C illustrates an exploded, perspective view of an example of a monitoring device including a sensor holder device, according to at least one example.

FIGS. 8A-8C illustrate example monitoring devices 800a-800c including various sensor holder devices 802a-802c, according to certain examples. The monitoring device 800 is an example of the monitoring device 100 described herein. Thus, the monitoring device 800 may include a top enclosure 820, a biosensor 804, a PCB 812, a bottom enclosure 822, and a sensor wire 806.

In the example illustrated in FIG. 8A, the sensor holder device 802a may be aligned with respect to the other components of the biosensor 804a such that the sensor wire 806a extends through an inner region of the biosensor 804a. For example, the sensor wire 806a may extend through an opening in the PCB 812a disposed within an inner region of the PCB 812a. An enclosure opening 824a of the bottom enclosure 822a may correspond to the opening in the PCB 812a.

In the example illustrated in FIG. 8B, the sensor holder device 802b may be aligned with respect to the other components of the biosensor 804b such that the sensor wire 806b extends through outer region of the biosensor 804b. For example, the sensor wire 806b may extend through a PCB opening 854b disposed within an outer region of the PCB 812b. An enclosure opening 824b of the bottom enclosure 822b may correspond to the PCB opening 854b.

In the example illustrated in FIG. 8CB, the sensor holder device 802c may be aligned with respect to the other components of the biosensor 804c such that the sensor wire 806c extends proximate to an outer perimeter of the biosensor 804c. For example, the sensor wire 806c may extend proximate to a perimeter edge 856c of the PCB 812c. In some examples, the perimeter edge 856c may include a cut-away portion 858c to accommodate the sensor wire 806c. The bottom enclosure 822c may include a corresponding cut-away portion 860c.

Figure 9:
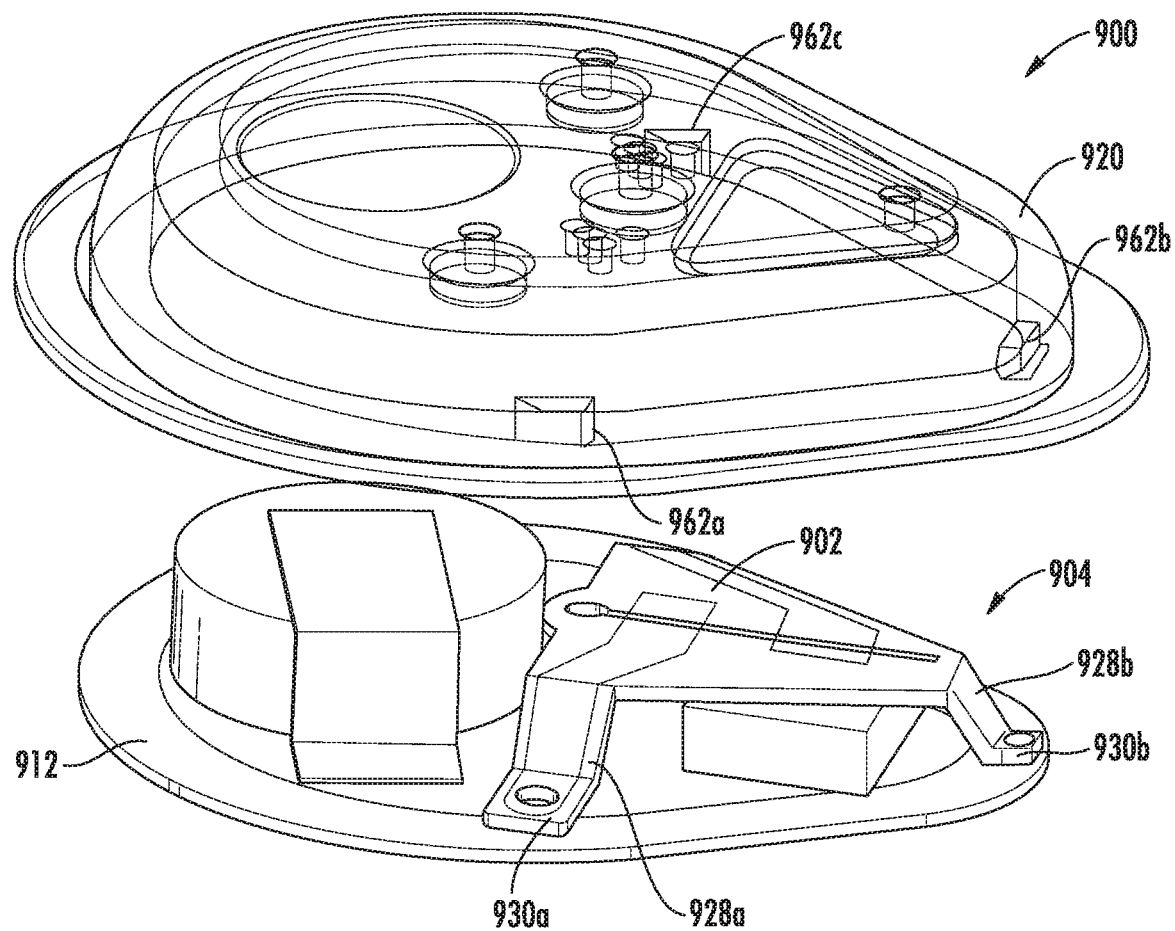
FIG. 9 illustrates an exploded, perspective view of an example of a monitoring device including a sensor holder device, according to at least one example.

FIG. 9 illustrates a monitoring device 900, according to at least one example. The monitoring device 900 is an example of the monitoring device 100. Thus, the monitoring device 900 may include a sensor holder device 902, a biosensor 904, and a top enclosure 920. In the example illustrated in FIG. 9, features of the sensor holder device 902 may be used to align the top enclosure 920 with the other portions of the monitoring device 900. For example, legs 928 and/or feet 930 of the sensor holder device 902 may correspond to alignment notches 962 of the top enclosure 920. During installation, the top enclosure 920 may be brought into contact with the sensor holder device 902 such that the legs 928 are received into the alignment notches 962. In some examples, alignment using the alignment notches 962 and portions of the sensor holder device 902 may result in a tighter fit between the top enclosure 920 and the other portions of the monitoring device 900. This may be because the manufacturing tolerances of the sensor holder device 902 are much tighter (e.g., +/−15 microns), which may result in an overall better fit.

As an alternative, the top enclosure 920 may be aligned with a perimeter edge of a PCB 912. Typically, the PCB 912 will be cut using a die, which may have a relatively high tolerance (e.g., +/−200 microns). This may result in a looser fit when compared to alignment using the alignment notches 962 and the legs 928.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:
1. A biosensor holder device, comprising:
a body;
a set of printed circuit board (PCB) mounting features attached to the body and extending from one side of the body;
a sensor guiding opening on a side of the body, wherein the body comprises a groove that extends from the sensor guiding opening and is sized to accommodate a sensor; and
an electrically conductive material extending between the groove and a distal end of a first PCB mounting feature of the set of PCB mounting features, wherein the sensor guiding opening is configured to receive a first portion of the sensor and guide the first portion of the sensor below the body and into the groove, wherein the groove is configured to retain a second portion of the sensor below the body, and wherein the electrically conductive material is positioned in the groove to electrically couple with the second portion of the sensor.

2. The biosensor holder device of claim 1, wherein the groove defines: a first region having a first cross-sectional area and sized to accommodate the first portion of the sensor; and a second region having a second cross-sectional area and sized to accommodate the second portion of the sensor, the first cross-sectional area being different from the second cross-sectional area.

3. The biosensor holder device of claim 1, wherein the sensor guiding opening intersects with the groove.

4. The biosensor holder device of claim 1, wherein the sensor holder device has a height measured from the body to the distal end of the first PCB mounting feature of 3 mm or less.

5. The biosensor holder device of claim 1, wherein the body has been formed from a first material using an injection molding technique.

6. A wearable monitoring device comprising:
a sensor having a distal portion and a proximal portion;
a printed circuit board having sensing circuitry mounted thereon;
a housing containing the printed circuit board and the proximal portion of the sensor, wherein the housing comprises a substantially planar bottom surface to allow the wearable monitoring device to be placed on a person's skin;
a sensor holder contained inside the housing that is electrically and mechanically coupled to the printed circuit board, the sensor holder comprising a top surface and a bottom surface, wherein the bottom surface faces the substantially planar bottom surface of the housing of the wearable monitoring device;
a groove in the bottom surface of the sensor holder in which the proximal portion of the sensor is retained;
electrical contacts associated with the groove electrically interfacing with electrodes on the proximal portion of the sensor, wherein the electrical contacts are electrically coupled to the printed circuit board; and
wherein the distal portion of the sensor is configured to extend substantially perpendicular to the substantially planar bottom surface of the housing into the person's skin, and wherein the sensor bends to extend substantially horizontally inside the housing and into the groove.

7. The wearable monitoring device of claim 6, wherein the sensor holder has a height of 3 mm or less.

8. The wearable monitoring device of claim 6, wherein the sensing circuitry comprises a battery, and wherein a height of the sensor holder is less than a height of the battery.

9. The wearable monitoring device of claim 6, wherein the top surface of the sensor holder is adapted to be grasped by a suction head of a robotic placement device.

10. The wearable monitoring device of claim 6, wherein the groove comprises an end wall.

11. The wearable monitoring device of claim 10, wherein an end of the proximal portion of the sensor is positioned adjacent to the end wall.

12. The wearable monitoring device of claim 6, wherein the sensor is retained in the groove by snap fit.

13. The wearable monitoring device of claim 6, wherein the housing comprises alignment features that contact the sensor holder.

14. A wearable monitoring device comprising:
a sensor having a distal portion and a proximal portion;
a printed circuit board having sensing circuitry mounted thereon;
a housing containing the printed circuit board and the proximal portion of the sensor, wherein the housing comprises a substantially planar bottom surface to allow the wearable monitoring device to be placed on a person's skin;
a sensor holder contained inside the housing electrically and mechanically coupled to the printed circuit board;
a groove in the sensor holder in which the proximal portion of the sensor is retained; and
electrical contacts associated with the groove electrically interfacing with electrodes on the proximal portion of the sensor, wherein the electrical contacts are electrically coupled to the printed circuit board, and wherein the electrical contacts comprise tabs that laterally deflect to accommodate and retain the sensor in the groove.

15. The wearable monitoring device of claim 14, wherein the sensor holder includes a top surface and a bottom surface, wherein the bottom surface faces the substantially planar bottom surface of the housing of the wearable monitoring device, and wherein the groove in the sensor holder extends upward from the bottom surface of the sensor holder.

* * * * *